(12) United States Patent
Bhosle et al.

(10) Patent No.: US 6,833,259 B2
(45) Date of Patent: Dec. 21, 2004

(54) 'PSEUDOMONAS STUTZERI' STRAIN AND PROCESS FOR PREPARATION OF XYLANASE

(75) Inventors: Narayan Baburao Bhosle, Goa (IN); Asha Giriyan, Goa (IN)

(73) Assignee: Council of Scientific and Industrial Research, New Delhi (IN)

( * ) Notice: Subject to any disclaimer, the term of this patent is extended or adjusted under 35 U.S.C. 154(b) by 158 days.

(21) Appl. No.: 10/223,852

(22) Filed: Aug. 20, 2002

(65) Prior Publication Data

US 2003/0008379 A1 Jan. 9, 2003

Related U.S. Application Data

(63) Continuation of application No. 09/811,753, filed on Mar. 19, 2001, now abandoned.

(51) Int. Cl.[7] ............................. C12N 1/20; C12N 9/24
(52) U.S. Cl. .................... 435/200; 435/253.3; 435/875
(58) Field of Search ............................ 424/200, 253.3, 424/875

(56) References Cited

U.S. PATENT DOCUMENTS

| | | | |
|---|---|---|---|
| 3,654,082 A | 4/1972 | Abdullah | 435/98 |
| 4,828,994 A | 5/1989 | Fahnestock et al. | 435/6 |
| 6,083,733 A | 7/2000 | Gronberg et al. | 435/200 |
| 6,127,329 A | 10/2000 | Baillely et al. | 510/320 |
| 6,180,382 B1 | 1/2001 | De Buyl et al. | 435/200 |

OTHER PUBLICATIONS

Okazaki, et al: "Production and properties of two types of xylanases from alkalophilic thermophilic Bacillus spp." *Applied Microbiology and Biotechnology*, vol. 19, pp. 335–340, (1984).

Tsujibo, et al: "Purification and properties of three types of xylanases produced by an alkalophilic actinomycete" *Journal of Applied Bacteriology*, vol. 69, pp. 398–405, (1990).

Dey, et al: "Purification and properties of extracellular endoxylanases from alkalophilic thermophilic Bacillus sp." *Canadian Journal of Microbiology*, vol. 38, pp. 436–442, (1992).

Rättö, et al: "Production of xylanolytic enzymes by an alkalitolerant *Bacillus circulans* strain" *Applied Microbiology and Technology*, vol. 37, pp. 470–473, (1992).

Bastawde, K. B.,.: "Xylan structure, microbial xylanases, and their mode of action" *World Journal of Microbiology and Biotechnology*, vol. 8, pp. 353–368 (1992).

Rodrigues, et al: "Exopolysaccharide production by *Vibrio fischeri*, a fouling marine bacterium" *Biofouling*, vol. 4, pp. 301–308, (1991).

Timell, T. E.: "Recent Progress in the Chemistry of Wood Hemicelluloses" *Wood Science and Technology*, vol. 1, pp. 45–70, (1967).

Viikari, et al.: "Xylanases in bleaching: From an idea to the industry" *FEMS Microbiology Review*, vol. 13, pp. 335–350, (1994).

Whistler, et al: "Hemicelluloses" *The Carbohydrates–Chemistry, Biochemistry*, II Ed., vol. 2A, pp. 447–469, (1980) Academic Press Inc, New York; Pigman and Horton, Editors.

Computer BRS Derwent DWPI Abstract 1997–112835 JP09000251 Meito Sangyo "Prod. Of Cholesterol Esterase by Culturing *Pseuodmonas stutzeri*, Useful for Determ. of Blood Cholesterol Conc." Jan. 7, 1997.

Computer BRS Derwent Abstract 1995–153779 SU1839184 Grishchenko et al "A Strain of the Bacterium *Pseudomonas stutzeri* is Used for Biochemical Purificn of Industrial Waters to Remove Aliphatic Amine(s)" Dec. 30, 1993.

Computer Derwent DWPI Abstract 1993–185137 Mercian Corp JP2932107 "Red Tide Control Agent–Contains *Pseudomonas stutzeri* Microorganisms and Opt. Clay Minerals Providing no Damage to e.g. Yellow Tail Fish" Aug. 9, 1999.

Computer Derwent DPWI Abstract 1993–098734 Arkadeva et al. "Strain of *Pseudomonas stutzeri* Bacteria is Used in Removing Maleic Acid From Industrial AQ. Wastes" Apr. 7, 19921.

*Primary Examiner*—Herbert J. Lilling
(74) *Attorney, Agent, or Firm*—Drinker Biddle & Reath LLP

(57) ABSTRACT

The present invention relates to a novel xylanase producing bacteria, *Pseudomonas stutzeri* deposited at the MCMRD, National Institute of Oceanography, Dona Paula, Goa 403004, India and having the assession number MCMRD-AB-001 and also deposited at the Agricultural Research Culture Collection (NRRL) International Depositary Authority, 1815 N. University Street, Peoria Ill. 61604, USA on Aug. 20, 2002 having accession No. NRRL B-30615, and a process for production of thermophilic and alkalophilic extracellular enzyme xylanase using the said bacteria.

24 Claims, 4 Drawing Sheets

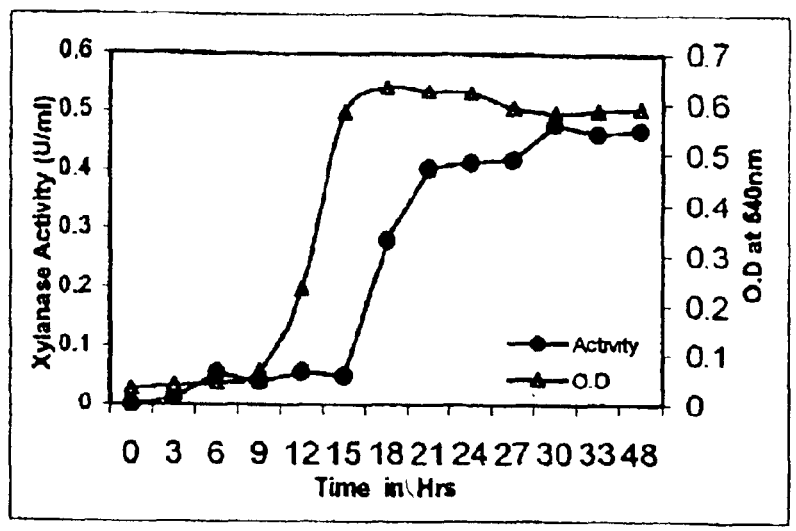
Fig.1. Time course of growth and enzyme production by *Pseudomonas stutzeri* cells were grown in a BSS medium containing birchwood xylan, pH 10. Growth was monitored by measuring optical density at 540nm. Xylanase activity was measured from cell free culture supernatant fluid. Δ ,O.D; ●, Activity

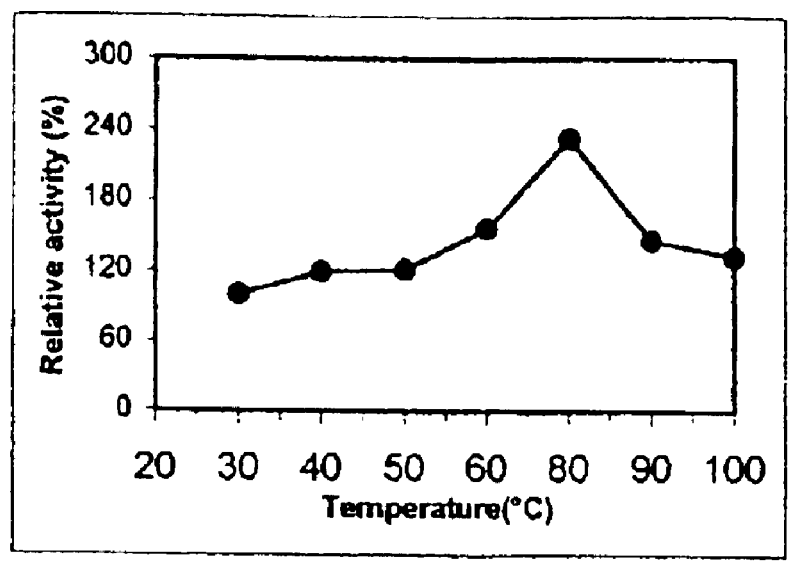
Fig.2. Effect of temperature on xylanase activity. The reaction was carried out at pH 9.5 for 10 mins.

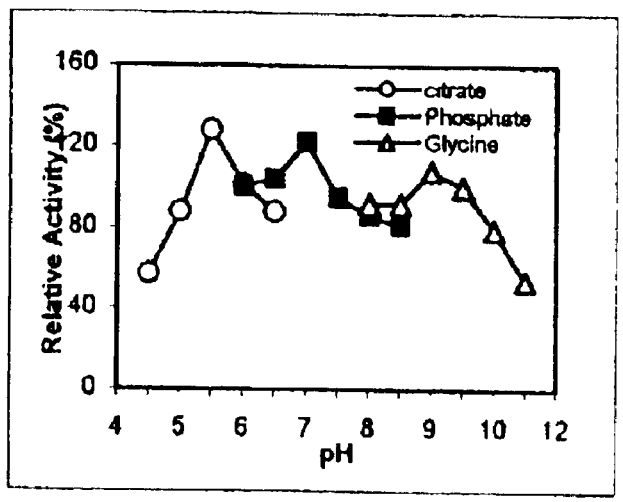

Fig. 3. pH Profile of *Pseudomonas stutzeri* xylanase. Enzyme activity was measured at 80°C and different pH values. The buffers used, each at a concentration of 50mM were :O,citrate; ■, phosphate; △, Glycine-NaoH.

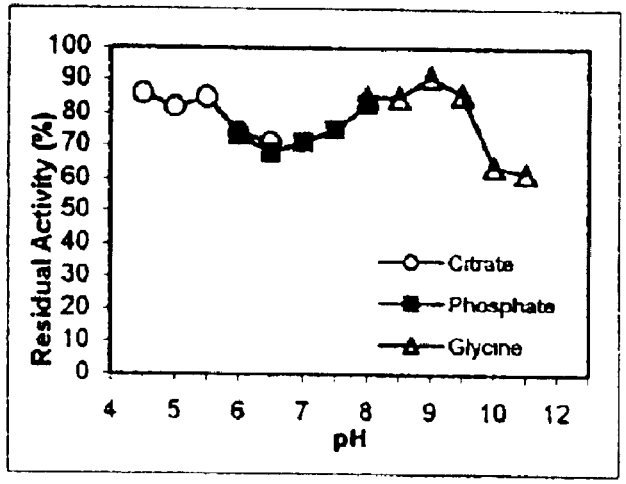

Fig.4. Effect of pH on xylanase stability. The enzyme was diluted with different buffers of varying pH values and incubated at 80°C for 30 min. Residual activity was assayed at pH 9.5 and 80°C The buffers used, each at a concentration of 50mM were: O,citrate; ■,phosphate; △,Glycine-NaoH.

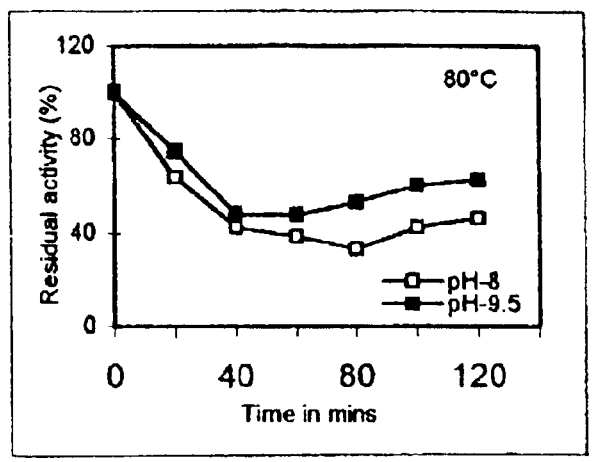

Fig.5. Thermal stability of *Pseudomonas stutzeri* xylanase at 80°C. The crude enzyme was diluted in 50mM phosphate buffer, ☐ pH 8 and Glycine -NaoH buffer, ■ pH 9.5, and heated at 80°C for 120 min. samples were withdrawn at time intervals and residual activity measured at 80°C, pH 9.5.

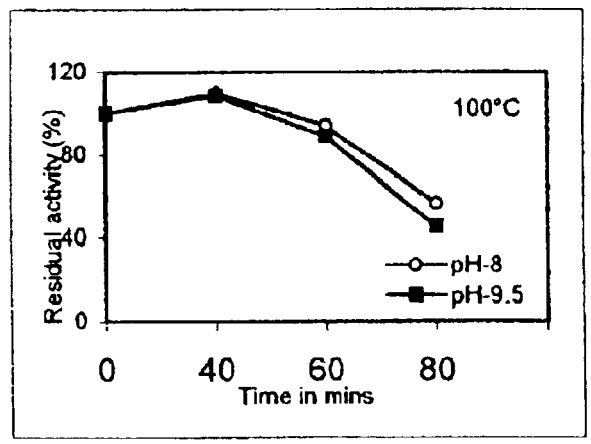

Fig.6. Thermal stability of *Pseudomonas stutzeri* xylanase at 100°C. The crude enzyme was diluted in 50mM, phosphate buffer, ☐ pH 8 and Glycine -NaoH buffer, ■ pH 9.5 and heated at 100°C samples were withdrawn at time intervals and residual activity measured at 80°C, pH 9.5

'PSEUDOMONAS STUTZERI' STRAIN AND PROCESS FOR PREPARATION OF XYLANASE

This application is a continuation of U.S. patent application Ser. No. 09/811,753 filed Mar. 19, 2001, abandoned.

FIELD OF INVENTION

The present invention relates to a novel xylanase producing bacteria, Pseudomonas stutzeri, deposited at the MCMRD, National Institute of Oceanography, Dona Paula, Goa 403004, India and having the accession number MCMRD- AB-001 and also deposited at the Agricultural Research Culture Collection (NRRL) International Depositary Authority, 1815 N. University Street, Peoria Ill. 61604, USA on Aug. 20, 2002 under accession No. NRRL B-30615. The invention also relates to a process for production of thermophilic and alkalophilic extracellular enzyme xylanase using said bacteria.

BACKGROUND OF THE INVENTION AND PRIOR ART DESCRIPTION

Xylan is the major component of plant hemicellulose present in angiosperm cell walls (Timell 1967). It is probably the second most abundant carbohydrate polymer of plants. Xylans are heterogeneous polysaccharides consisting of a backbone of 1,4-linked D-xylopyranosyl residues that often have O-acetyl, arabinosyl, and methylglucuronosyl substituents (Whistler & Richards 1970). A wide variety of microorganisms are known to produce xylanases, which are enzymes that are involved in the hydrolysis of xylan (Bastawade 1992).

In recent years, increasing attention has been given to the study of xylan-degrading enzymes because of their potential application in different industrial processes. One area of application is in the pulp and paper industry where xylanase can be used for the bleaching of kraft pulps (Viikari et al. 1994). The use of xylanase prior to normal bleaching operations has been shown to significantly reduce the amount of chlorinated organic compounds formed during the bleaching process (Senior et al. 1992).

Plant biomass is subjected to kraft pulping for use in pulp and paper industry. During kraft pulping, extensive modification of the hemicellulose component of plant biomass takes place. Because of the highly alkaline conditions during the kraft cook, part of the xylan dissolves in the pulping liquor, whereas short chain xylan precipitates in more or less crystalline form on the surface of cellulose microfibrils. This xylan forms a barrier against effective chemical extraction of residual brown colored lignin from the fibers. As a result, large quantities of chlorine or chlorine-containing compounds are required so as to reduce the kappa number, and to increase the pulp brightness. Discharge of wastewater containing large quantities of chlorine or chlorine-containing compounds may cause environmental problems. Therefore efforts have been made to develop environmentally friendly technologies. Solubilization of the hemicellulose settled on the pulp fibres by enzyme treatment is one such method. Such enzyme treatment would improve the accessibility of the brown lignin to chemical treatment thereby reducing the quantities of bleaching chemicals but maintaining the same level of brightness. For successful development of enzyme technology for pulp and paper industries, the first requirement is to have an enzyme which is active at high alkaline pH and temperature. There are a number of reports on thermophilic xylanase isolated from bacteria. However most of these xylanases are active in slightly acidic conditions between pH 4 to 6 and a temperature below 70° C. Due to high temperature and alkalinity of the pulp during processing, more thermophilic and alkalophilic xylanases are preferred over the currently used ones.

Since the kraft process of pulp and papermaking is carried out at alkaline pH and high temperature, the use of alkaline xylanase with higher temperature optima is considered to be advantageous. Alkaline xylanase will also find a number of other applications. For example, because of high solubility of xylan at alkaline pH, alkaline xylanase may have good potential for the hydrolysis of hemicellulosic waste to fermentable sugars.

(i) A reference may be made to the publication of Okazaki W, Akiba T, Horikoshi K, Akahoshi R, 1984. Production and properties of two types of xylanases from alkaliphilic thermophilic Bacillus sp. Applied Microbiology & Biotechnology, 19: 335–340.

(ii) Another reference may be made to the publication of Tsujibo H, Sakamoto T, Nishino N, Hasegawa T, Inamori Y, 1990. Purification and properties of three types of xylanases produced by an alkaliphilic actinomycete. Journal of Applied Bacteriology, 69: 398–405.

(iii) Still another reference may be made to the publication of Dey D, Hinge J, Shendye A & Rao M, 1992. Purification and properties of extracellular endoxylanases from alkalophilic thermopbilic Bacillus sp. Canadian Journal of Microbiology, 38: 436–442.

(iv) Yet another reference may be made to the publication of Ratto M, Poutman K & Viikari I, 1992. Production of xylanolytic enzymes by an alkalitolerant Bacillus cirulans strain. Applied Microbiology and Biotechnology, 37: 470–473.

(v) One more reference may be made to a publication by Bastawade K B, 1992. Xylan structure, microbial xylanases and their mode of action. World Journal of Microbiology and Biotechnology, 8:353–368.

(vi) Another reference may be made to a publication by Rodrigues C and Bhosle N B, 1991. Exopolysaccharide production by Vibrio fischeri, a fouling marine bacterium. Biofouling, 4: 301 –308,1991.

(vii) Further reference may be made to a publication by Senior D J, Hamilton J, Bernier R L, Manoir J, 1992. Reduction of chlorine use during bleaching of kraft pulp following xylanase treatment. Tappi Journal ,75: 125–130.

(viii) Another reference may be made to a publication of Timell T E, 1967. Recent progress in the Chemistry of wood hemicellulose. Wood Sci. Technol, 1: 45–70.

(ix) Still another reference may be made to a publication by Viikari I, Kantelinen A, Sundquist J and Linko M, 1994. Xylanases in bleaching: From an idea to industry. FEMS Microbiology Review, 13 : 335–350.

(x) Yet another reference may be made to a publication by Whistler R L & Richards E L, 1970. Hemicelluloses, In: Pigman W & Horton D (ed), The carbohydrateschemistry and biochemistry, 2nd ed. Vol 2A. Academic Press, Inc., New York.

(xi) One more reference may be made to U.S. Pat. No. 6,083,733 by Gronberg et al.

(xii) One another reference may be made to U.S. Pat. No. 6,180,382 by De Buyl et al.

(xiii) Further reference may be made to U.S. Pat. No. 4,8248,994 by Fahnestock et al.

However, xylanases produced from most of the above alkalophilic strains have their optimum pH around neutrality. Further, most of these xylanases studied are active in slightly acidic conditions between pH 4 and 6 and temperature below 70° C. Due to high temperature and alkalinity of the pulp during pulp processing more thermophilic and alkalophilic xylanases are preferred over the currently used ones.

OBJECTS OF THE INVENTION

The main object of the present invention is to provide a novel xylanase-producing bacteria strain *Pseudomonas stutzeri*, which is deposited at the MCMRD, National Institute of Oceanography, Dona Paula, Goa 403004, India and having the accession number MCMRD-AB-001.

Another object of the present invention is to provide a process for the preparation of alkalophilic and thermophilic extracellular enzyme xylanase from the said bacteria.

Another object of the present invention is to provide an alkalophilic and thermophilic xylanase showing activity at higher pH values.

Still another object of the present invention is to provide an alkalophilic and thermophilic xylanase showing activity at high temperatures.

SUMMARY OF THE INVENTION

The present invention relates to a novel xylanase-producing bacteria strain *Pseudomonas stutzeri* deposited at the MCMRD, National Institute of Oceanography, Dona Paula, Goa 403004, India and having the accession number MCMRD-AB-001, and also deposited at the Agricultural Research Culture Collection (NRRL) International Depositary Authority, 1815 N. University Street, Peoria Ill. 61604, USA under accession No. NRRL B-30615 on Aug. 20, 2002. The invention also relates to a process for production of thermophilic and alkalophilic extracellular xylanase from the bacteria.

DETAILED DESCRIPTION OF THE INVENTION

Accordingly, the present invention provides a novel bacteria strain *Pseudomonas stutzeri* capable of producing xylanase, which strain is deposited at the MCMRD, National Institute of Oceanography, Dona Paula, Goa 403004, India, and which has the accession number MCMRD-AB-001.

In an embodiment of the present invention, the novel bacteria strain *Pseudomonas stutzeri* was isolated from the sediment biofilm developed on mild steel panels immersed in coastal waters of the Arabian Sea.

In another embodiment of the present invention, the bateria strain *Pseudomonas stutzeri* is gram negative, smooth, off-white, opaque, circular and entire.

In still another embodiment of the present invention, the bacteria *Pseudomonas stutzeri* is not easily dispersed and butyrous.

In yet another embodiment of the present invention, the bacteria comprises the owing physiological characteristics:

| Physiology at 28° C. | |
|---|---|
| Morphological/Biochemical Test | Reaction |
| Catalase | + |
| Oxidase | + |
| Hugh & Leifson | Oxidative |
| Voges-Proskauer test | − |

-continued

| Physiology at 28° C. | |
|---|---|
| Morphological/Biochemical Test | Reaction |
| Indole | − |
| Peptone Water sugars | |
| Mannose | − |
| Inositol | − |
| Glucose | − |
| Sorbitol | − |
| Sucrose | − |
| Mellibiose | − |
| Gelatin hydrolysis | + |
| Urease | − |
| $H_2S$ | − |
| Orthonitrophenolgalactosidase | − |
| Arginine dihydrolase | − |
| Citrate | − |

(− = Negative; + = Positive)

The present invention also provides a process for the preparation of alkalophilic and thermophilic extracellular enzyme xylanase from the a the novel bacteria *Pseudomonas stutzeri*. The process comprises cultivating *Pseudomonas stutzeri* in a conventional nutrient medium, separating cells from the supernatant by any conventional method followed by recovery and purification of the xylanase from the supernatant by any conventional method.

In an embodiment of the present invention, the xylanase shows activity at pH values between 5.5 and 9.5, and a temperature of 80° to 100° C.

In another embodiment of the present invention, the xylanase is capable of retaining 42% of its activity when sterilized at 120° C. and 15 lb pressure for 10 minutes.

In still another embodiment of the present invention, the activity of xylanase is 250 times greater than the activity shown at 30° C.

In yet another embodiment of the present invention, the nutrient medium contains an assimilable nitrogen source, conventional trace elements and a carbon source.

In one more embodiment of the present invention, the nutrient medium has 30.0 g NaCl, 0.75 g Kcl, 7.0 g $MgSO_4$, 1.0 g $NH_4Cl$, 7.0 ml of 10% $K2HPO_4$, 3 ml of 10% $KH_2PO_4$ and 1.0 ml of trace metal solution dissolved in 1000 ml of distilled water.

In one another embodiment of the present invention, the trace metal solution contains 2.85 g/l $H_3BO_3$, 1.80 g/l $MnCl2.7 H2O$, 2.49 g/l $FeSO4.7 H_2O$, 1.77 g/l Na-Tartarate, 0.03 g/l $CUCl_2$, 0.02 g/l $ZnCl_2$, 0.04 g/l $CoCl_2$, and 0.02 g/l $Na_2MoO_4.2 H_2O$ dissolved in 1000 ml of distilled water.

In an embodiment of the present invention, pH of the nutrient medium is between 9 and 10.

In another embodiment of the present invention, the carbon source of the medium is selected from the group comprising of xylan, xylose, galactose and sucrose.

In still another embodiment of the present invention, 0.1% W/V of xylan is added as the carbon source.

In yet another embodiment of the present invention *Pseudomonas stutzeri* was isolated from the sediment biofilm developed on mild steel panels immersed in coastal waters of the Arabian Sea. Its morphology and physiology can be summarised as follows (all temperatures in degrees centigrade):

Morphology on ZoBell Marine Agar at 28±2° C.

Gram—negative, motile coccobacilli, colonies: 1 mm, off-white, opaque, circular, entire, smooth, soft, not easily dispersed, and butyrous.

| Physiology at 28° C. | |
| --- | --- |
| Morphological/Biochemical Test | Reaction |
| Catalase | + |
| Oxidase | + |
| Hugh & Leifson | Oxidative |
| Voges-Proskauer test | − |
| Indole | − |
| Peptone Water sugars | |
| Mannose | − |
| Inositol | − |
| Glucose | − |
| Sorbitol | − |
| Sucrose | − |
| Mellibiose | − |
| Gelatin hydrolysis | + |
| Urease | − |
| $H_2S$ | − |
| Orthonitrophenolgalactosidase | − |
| Arginine dihydrolase | − |
| Citrate | − |

(− = Negative; + = Positive)

In one more embodiment of the present invention, the cultivation of *Pseudomonas stutzeri* is effected in batch culture.

In one other embodiment of the present invention, the microorganism can be cultivated under aerobic conditions.

In an embodiment of the present invention, the *Pseudomonas stutzeri* is grown at least for 28 hours at a temperature range of 25° to 35° C.

In another embodiment of the present invention, the *Pseudomonas stutzeri* is grown at 28° to 30° C.

In still another embodiment of the present invention, the xylanase enzyme production is enhanced during the stationary growth phase of the organism.

In yet another embodiment of the present invention, the xylanase production is growth-associated.

In one more embodiment of the present invention, the xylanase production reached a maximum after 24 h.

In one another embodiment of the present invention, the enzyme production remained more or less the same for up to 22 days, while biomass showed a marginal decrease.

In an embodiment of the present invention, a significant amount of xylanase was also produced when xylose was used as carbon source. However, compared to xylan, lower xylanase activity was observed.

In another embodiment of the present invention, the xylanase is recovered from a cell-free supernatant by precipitation.

In still another embodiment of the present invention, the xylanase is purified using conventional dialysis techniques.

In yet another embodiment of the present invention, the extracellular xylanase may be isolated from the culture supernatant (free from cells) by precipitation with 70% ammonium sulphate dissolved in glycine-NaOH buffer having a pH of 9.5.

In one more embodiment of the present invention, the xylanase is deionized by using dialysis bags (1 MW cut off of 8000 daltons).

In one another embodiment of the present invention, the isolated material can be used as a source of enzyme after dialysis.

BRIEF DESCRIPTION OF THE ACCOMPANYING DRAWINGS

In the drawings accompanying the specification,

FIG. 1 represents time course of growth and enzyme production by *Pseudomonas stutzeri* cells when grown in a BSS medium containing birchwood xylan, pH 10.

FIG. 2 represents the effect of temperature on xylanase activity when the reaction is carried out at pH 9.5 for 10 minutes.

FIG. 3 represents a pH profile of *Pseudomonas stutzeri* xylanase activity. The enzyme activity was measured at 80° C. and different pH values.

FIG. 4 represents the effect of pH on xylanase stability. The enzyme is diluted with different buffers of varying pH values and incubated at 80° C. for 30 minutes. The residual activity was assayed at pH 9.5 and 80° C.

FIG. 5 represents the thermal stability of *Pseudomonas stutzeri* xylanase at 80° C.

FIG. 6 represents the thermal stability of *Pseudomonas stutzeri* xylanase at 100° C.

The following examples illustrate the present invention and therefore should not be construed to limit the scope of the present invention.

EXAMPLE 1

Extracellular xylanase production by *Pseudomonas stutzeri*: Extracellular xylanase production by *Pseudomonas stutzeri* was followed in a batch culture (FIG. 1). The culture was grown in a 250 milliliter flask containing sixty milliliters of growth medium as defined above, supplemented with 0.1 gram of xylan as a carbon source for 48 hours. Aeration was provided by shaking the culture flask at 150 RPM using a rotary shaker.

The logarithmic growth continued for 18 hours, and during this stage xylanase production could be detected (FIG. 1). Although xylanase production commenced during the exponential phase of growth, the production was highest during the stationary growth phase.

EXAMPLE 2

Precipitation and recovery of xylanase: *Pseudomonas stutzeri* was grown in the growth medium as defined above, supplemented with 0.1 grams of xylan as carbon source, for 48 hours. Cells were removed by centrifugation at 8000 RPM and 4° C. Xylanase enzyme was isolated from the cell-free supernatant by adding 70 grams of ammonium sulphate per 100 milliliters of the cell-free supernatant. The precipitated enzyme was collected using a spatula and dissolved in 50 mM glycine-NaOH buffer, pH 9.5. The enzyme solution was dialysed overnight using the 50 mM glycine-NaOH buffer pH 9.5. The obtained dialysed solution of the enzyme was used to characterize the activity of the xylanase enzyme.

EXAMPLE 3

Effect of pH on xylanase activity and stability: The effect of pH on the activity of the xylanase enzyme was studied using 50 mM sodium citrate (pH 4 to 6), 50 mM phosphate (pH 6 to 8) and 50 mM glycine-NaOH (pH 7.5 to 11) buffers. In order to assess the stability of the enzyme at various pHs, one volume of the enzyme solution was mixed with one volume of the above buffer solution having different pHs (5 to 11) and incubated for 30 minutes. The enzyme showed three activity maxima at pH 5.5, 7, and 9.0 (FIG. 2). Stability studies showed that the enzyme was more stable at the alkaline pH of 8 (FIG. 3).

EXAMPLE 4

Effect of temperature on the xylanase activity and stability: The effect of temperature was studied by assessing the activity of the enzyme at various temperatures ranging from 30 to 100° C. The enzyme activity increased with the increase in temperature (FIG. 4). The enzyme showed highest activity at 80° C., and then showed some decrease, as the temperature was further increased to 100° C. The activity of the enzyme at 80° C. was higher by a factor of about 250 as compared to that observed at 30° C. When the enzyme solution in a glycine-NaOH buffer of pH 9.5 was heated for 2 hours at 800 C (FIG. 5), 63% activity was retained. When the enzyme solution in glycine-NaOH buffer was heated for 80 minutes at 100° C., 45% enzyme activity was retained (FIG. 6).

EXAMPLE 5

Effect of sterilisation on xylanase activity: When the enzyme solution in glycine buffer of pH 9.5 was sterilized for 10 minutes at 120° C. and 15 lb pressure, the enzyme retained 42% of its activity (Table 1).

TABLE 1

Effect of sterilization (Pressure 15 lbs; Temperature 121° C.) for 10 minutes on xylanase activity.

| Initial Activity ($\mu$/mol/min/ml) | After Sterilization (15 lb, 121° C.) ($\mu$/mol/min/ml) | Residual Activity |
|---|---|---|
| 6.49 | 2.73 | 42.06 |

EXAMPLE 6

Effect of carbon sources on xylanase activity: The effect of various carbon sources on the xylanase production was assessed by culturing *Pseudomonas stutzeri* for 48 hours in 50 milliliters of growth medium as defined above, containing 0.1 grams of either xylan, xylose, arabinose, glucose, sucrose, galactose, cellobiose or carboxymethylcellulose as carbon source. Cells were removed by centrifugation and the supernatant solution was used to estimate the activity of the enzyme. Of these, xylose produced a higher amount of xylanase as compared to other sugars but relatively less than that obtained with xylan (Table 2). The other natural sources of xylan can also be utilised for the production of xylanase.

TABLE 2

Effect of different sugars on xylanase activity

| Sugars (0.1%) | Activity ($\mu$/mol/min/ml) |
|---|---|
| Arabinose | 0.43 |
| Cellobiose | 0.85 |
| Carboxymethylcellulose | 0.51 |
| Galactose | 1.60 |
| Glucose | 0.45 |
| Sucrose | 1.54 |
| Xylan | 4.43 |
| Xylose | 2.10 |

EXAMPLE 7

Effect of metal ions on xylanase activity: The effect of metal ions Ca, Mg, Fe, Hg, and Cu, and EDTA, on the activity of xylanase was evaluated. Twenty microliters of xylanase enzyme was mixed 1 mM of either Ca, Mg, Fe, Hg, Cu or EDTA for 30 min and the enzyme activity was measured. Ca, Mg, Fe, Cu, and EDTA did not inhibit the activity of the enzyme. Hg inhibited the enzyme activity (Table 3).

TABLE 3

Effect of ions and chelator on xylanse activity

| Metal Ion (1 mM) | Activity ($\mu$/mol/min/ml) |
|---|---|
| $CaCl_2$ | 8.56 |
| $MgSO_4$ | 7.00 |
| $FeSO_4$ | 5.80 |
| $CuSO_4$ | 3.60 |
| $HgCl_2$ | 0.68 |
| EDTA | 8.20 |

What is claimed is:

1. An isolated bacteria strain *Pseudomonas stutzeri* having accession number NRRL-B-30615.

2. A process for the preparation of alkalophilic and thermophilic extracellular xylanase from the bacteria strain *Pseudomonas stutzeri*, said strain having the accession number NRRL-B-30615, said process comprising cultivating the *Pseudomonas stutzeri* in a nutrient medium, separating cells from the culture supernatant, and recovering and purifying the xylanase from the supernatant.

3. A process as claimed in claim 2, wherein the xylanase has activity at pH values between 5.5 and 9.5, and at temperatures of 80° to 100° C.

4. A process as claimed in claim 2, wherein the xylanase is capable of retaining 42% of its activity when sterilized at 120° C. and 15 lb pressure for 10 minutes.

5. A process as claimed in claim 2, wherein the activity of the xylanase is 250 times greater than its activity at 30° C.

6. A process as claimed in claim 2, wherein the nutrient medium contains an assimilable nitrogen source, conventional trace elements and a carbon source.

7. A process as claimed in claim 2, wherein the nutrient medium contains 30.0 g NaCl, 80.75 g KCl, 7.0 g $MgSO_4$, 1.0 g $NH_4Cl$, 7.0 ml of 10% $K_2HPO_4$, 3 ml of 10% $KH_2PO_4$ and 1.0 ml of trace metal solution dissolved in 1000 ml of distilled water.

8. A process as claimed in claim 2, wherein the trace metal solution contains 2.85 g/l $H_3BO_3$, 1.80 g/l $MnCl_2.7\ H_2O$, 2.49 g/l $FeSO_4.7\ H_2O$, 1.77 g/l Na-Tartarate, 0.03 g/l $CuCl_2$, 0.02 g/l $ZnCl_2$, 0.04 g/l $CoCl_2$, and 0.02 g/l $Na_2MoO_4.2\ H_2O$ dissolved in 1000 ml of distilled water.

9. A process as claimed in claim 2, wherein the pH of the nutrient medium is between 9 and 10.

10. A process as claimed in claim 2, wherein the medium contains a carbon source selected from the group comprising of xylan, xylose, galactose and sucrose.

11. A process as claimed in claim 2, wherein 0.1% w/v of xylan is the carbon source.

12. A process as claimed in claim 2, wherein the cultivation of *Pseudomonas stutzeri* is effected in batch culture.

13. A process as claimed in claim 2, wherein the bacteria *Pseudomonas stutzeri* is cultivated under aerobic conditions.

14. A process as claimed in claim 2, wherein the bacteria *Pseudomonas stutzeri* is grown at least for 28 hours at a temperature range of 25° to 35° C.

15. A process as claimed in claim 2, wherein the bacteria *Pseudomonas stutzeri* is grown at 28° to 30° C.

16. A process as claimed in claim 2, wherein the xylanase enzyme production is enhanced during the stationary growth phase of the bacteria *Pseudomonas stutzeri*.

17. A process as claimed in claim 2, wherein the xylanase production is associated with the growth of the bacteria *Pseudomonas stutzeri*.

18. A process as claimed in claim 2, wherein the xylanase production reaches maximum level after 24 h cultivation.

19. A process as claimed in claim 2, wherein the enzyme production remains substantially constant up to 22 days growth while biomass is marginally decreased.

20. A process as claimed in claim 2, wherein xylose is the carbon source.

21. A process as claimed in claim 2, wherein the xylanase is recovered from the supernatant by precipitation.

22. A process as claimed in claim 2, wherein the xylanase is purified by dialysis.

23. A process as claimed in claim 2, wherein the extracellular xylanase is isolated from the supernatant by precipitation with 70% ammonium sulphate dissolved in glycine-NaOH buffer having a pH of 9.5.

24. A process as claimed in claim 2, wherein the xylanase is deionized by dialysis using dialysis bags having a molecular weight cut off of 8000 dalton.

* * * * *